United States Patent
Soykan et al.

(10) Patent No.: US 7,349,740 B2
(45) Date of Patent: Mar. 25, 2008

(54) MYOCARDIAL STIMULATION

(75) Inventors: Orhan Soykan, Shoreview, MN (US); Donovan G. Maura, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 182 days.

(21) Appl. No.: 10/896,760

(22) Filed: Jul. 22, 2004

(65) Prior Publication Data

US 2005/0043766 A1 Feb. 24, 2005

Related U.S. Application Data

(60) Provisional application No. 60/490,659, filed on Jul. 28, 2003.

(51) Int. Cl.
*A61N 1/00* (2006.01)
(52) U.S. Cl. ............................. 607/50; 607/3
(58) Field of Classification Search .................. 607/9, 607/2–3, 50; 604/20
See application file for complete search history.

(56) References Cited

U.S. PATENT DOCUMENTS

| 6,151,525 | A | 11/2000 | Donovan et al. ............. 697/50 |
| 6,597,952 | B1 | 7/2003 | Belsky Ziv et al. ........... 607/27 |
| 2002/0124855 | A1 | 9/2002 | Chachques .................. 128/898 |
| 2003/0074029 | A1* | 4/2003 | Deno et al. .................... 607/23 |

FOREIGN PATENT DOCUMENTS

| WO | WO 97/35636 | 10/1997 |
| WO | WO 02/49669 | 6/2002 |

OTHER PUBLICATIONS

Chiu, RC-J, et al., Cellular cardiomyoplasty: myocardial regeneration with satellite cell implantation, Annual Thoracic Surgery; 60:12-8 (1995).
Jain M., et al., Cell therapy attenuated deleterious ventricular remodeling and improves cardiac performance after myocardial infarction, Circulation, 2001; 103:1920-7.
Kao, Race L., et al., Satellite cell transplantation to repair injured myocardium, Cardiac and Vascular Regeneration, 1:31-42 (2000).
Murray, C.E., et al., Skeletal myoblast transplantation for repair of myocaridal necrosis, Journal Clinical Invest. 1996; 98:2512-23.
International Preliminary Report on Patentability dated Apr. 29, 2005, International Application No. PCT/US2004/023713.

* cited by examiner

*Primary Examiner*—Carl Layno
*Assistant Examiner*—Yun Haeng Lee
(74) *Attorney, Agent, or Firm*—Kenneth J. Collier (57) ABSTRACT

In general, the invention is directed to methods for electrically stimulating transplanted biological material, such as transplanted cells, to improve the performance of the heart during systole. In particular, the invention is directed to devices and techniques for stimulating biological material transplanted in a myocardium of a heart during an ejection phase of a cardiac cycle. The transplanted biological material may include cells, such as skeletal myoblasts, precursor cells, endothelial cells, differentiated or undifferentiated stem cells, undifferentiated contractile cells, fibroblasts and genetically engineered cells. In general, stimulation of the transplanted biological material during the ejection phase of the cardiac cycle, when the aortic and pulmonary valves are open, provides hemodynamic assistance to the heart.

33 Claims, 5 Drawing Sheets

MYOCARDIAL STIMULATION

This application claims the benefit of U.S. Provisional Application Ser. No. 60/490,659, filed Jul. 28, 2003, the entire content of which is incorporated herein by reference.

TECHNICAL FIELD

The present invention relates to systems and methods and implantable systems associated with the heart, and in particular, to systems and methods associated with stimulating the myocardium.

BACKGROUND

During coronary artery disease, formation of plaques narrows the lumen of the coronary artery, reducing the $O_2$ supply to cardiac tissue. If the coronary artery becomes occluded, the cardiac tissue served by the coronary artery soon dies from $O_2$ deprivation. Actual necrosis of heart tissue is called acute myocardial infarction, or heart attack.

Once the cardiac tissue has died, the tissue becomes infiltrated with noncontracting scavenger cells, which are ultimately replaced with fibrous scar tissue. The fibrous scar tissue, which includes fibroblasts and an extracellular matrix, does not significantly contribute to the contraction of the heart. Cardiac cells do not naturally repopulate the damaged region.

Cellular cardiomyoplasty involves transplanting cells into the damaged myocardium to repopulate the damaged region. In one procedure, cells are transplanted by injection directly into or proximate to the affected tissue. The transplanted cells are more elastic than the fibrous scar tissue, and therefore the presence of the cells enhances the elasticity of the heart. The elasticity provided by the cells improves the performance of the heart during diastole, which is the relaxing and filling phase of the cardiac cycle.

SUMMARY

In general, the invention is directed to methods for electrically stimulating transplanted biological material, such as transplanted cells, to improve the performance of the heart during systole. In particular, the invention is directed to devices and techniques for stimulating biological material transplanted in a myocardium of a heart during an ejection phase of a cardiac cycle.

The transplanted biological material may include cells, such as skeletal myoblasts, precursor cells, endothelial cells, differentiated or undifferentiated stem cells, undifferentiated contractile cells, fibroblasts and genetically engineered cells. The biological material may further comprise components of cells, such as genetic material, or a chemoattractant to attract precursor cells. Some of the biological material, such as skeletal cells, may be naturally contractile. It has been discovered that electrical stimulation may result in differentiation or phenotypic conversion, causing the biological material to become more contractile.

In a typical application, an implantable medical device (IMD) delivers a set of stimulating pulses to the transplanted biological tissue when contraction of the transplanted tissue will assist in hemodynamic function. In general, stimulation during the ejection phase of the cardiac cycle, when the aortic and pulmonary valves are open, provides hemodynamic assistance.

The invention encompasses various techniques for stimulating the biological material during the ejection phase. The IMD may, for example, time the delivery of the stimulations by observing an electrical signal generated by the heart, such as an R-wave. In some embodiments, the IMD may deliver pacing stimulations to the heart, and the IMD may time the delivery of the stimulations according to the paces. The IMD may also time the delivery of the stimulations according a biological signal detected by a sensor, such as a sound sensor, pressure sensor, impedance sensor, flow meter or accelerometer.

In one embodiment, the invention is directed to a method comprising electrically stimulating biological material transplanted in a myocardium of a heart during an ejection phase of a cardiac cycle. The transplanted biological material may be in, or proximate to, an infarct region of the myocardium. The stimulation may include a set of stimulating pulses.

In another embodiment, the invention is directed to a method that comprises electrically stimulating biological material transplanted in a myocardium of a heart during an ejection phase of a first cardiac cycle, suspending electrical stimulation of the biological material during the ejection phase of a second cardiac cycle and monitoring a hemodynamic parameter during the second cardiac cycle. The method also includes determining whether to electrically stimulate the biological material during the ejection phase of a third cardiac cycle as a function of the monitoring. This method can be used to determine whether the stimulations should be continued, discontinued, continued with a different stimulation therapy regimen, or whether physician intervention is indicated.

In other embodiments, the invention is directed to a computer-readable medium comprising instructions for causing a programmable processor to carry out the methods of the invention.

In a further embodiment, the invention is directed to a system that includes at least two electrodes to deliver electrical stimulation to biological material transplanted in a myocardium of a heart and a processor to control delivery of the stimulation during ejection phase of a cardiac cycle. The system may be embodied in a single IMD or in multiple devices. The system may also include a sensor to sense a biological signal and may also include the capability of delivering defibrillation therapy.

The invention may result in one or more advantages. Development of necrotic tissue causes the heart to become less elastic, and also can adversely affect hemodynamic function. It has been observed that biological material transplanted in or proximate to an infarct region of a heart improves the elasticity of the heart. Further, stimulation of the biological material according to the invention can improve the hemodynamic function of the heart, by causing contraction of at least a portion of the biological material, thereby contributing to the ejection of blood. Furthermore, application of the stimulation may speed up the formation of the contractile tissue and prevent the invasion of the infarct region by non-contractile fibroblasts.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
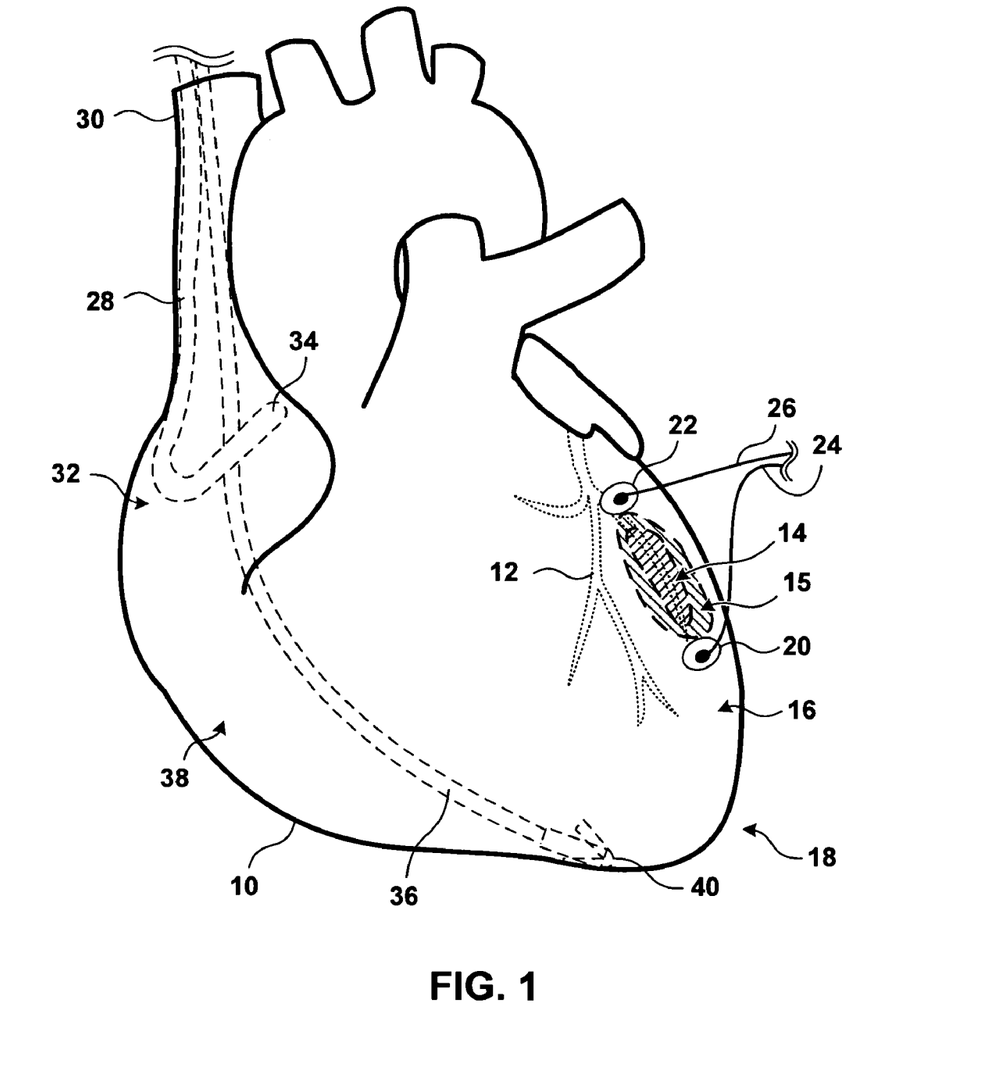
FIG. 1 is an illustration of a human heart showing deployment of leads and electrodes according to an embodiment of the invention.

FIG. 1 is a schematic diagram of a human heart 10. A blockage in a branch of coronary artery 12 has deprived region 14 of a blood supply, and consequently of oxygen. As a result, the myocardial tissue in region 14 has become damaged. In particular, some tissue has become necrotic, and an infarct region 14 has developed. In the example shown in FIG. 1, infarct region 14 is on the epicardium of the left ventricle 16.

Necrotic tissue does not contribute to the pumping action of heart 10. In particular, infarcted tissue does not contract in response to the excitation that takes place during a cardiac cycle. Normally, a ventricular excitation propagates from proximate to the apex 18 throughout the ventricular myocardium via gap junctions in the cardiac muscle, and the cardiac muscle contracts. The excitation does not cause infarct region 14 to contract, however. On the contrary, infarct region 14 can disrupt the propagation of the excitation, thereby affecting the excitation of healthy cardiac muscle. Moreover, scar tissue in infarct region 14 is usually less elastic than cardiac muscle, and can impair the function of heart 10 during the systolic and diastolic phases.

In the example of FIG. 1, a zone 15 proximate to infarct region 14 has been repopulated with transplanted biological material. The biological material, which may be transplanted into, transplanted proximate to or transplanted around the necrotic tissue, may include any of several biological substances, singly or in combination. The biological material may include cells, such as skeletal myoblasts, precursor cells, endothelial cells, differentiated or undifferentiated stem cells, undifferentiated contractile cells, fibroblasts and genetically engineered cells. The biological material may further comprise components of cells, such as genetic material, genetic vectors such as viruses, or proteins such as Insulin-Like Growth Factor or other growth factors. The biological material may also include a chemoattractant to attract precursor cells from the heart or from the other organs to repopulated zone 15 or infarct region 14. These categories of biological material are not exclusive of one another, and a particular element of biological material may belong to more than one category. Also, the transplanted biological material need not be exclusively biological, but may include an inorganic or engineered material, such as a scaffold to hold biological material. Furthermore, the invention is not limited to the particular materials listed herein.

Nor is the invention limited to any particular transplantation technique. For a typical patient, a surgeon may transplant biological material by injection during a surgical procedure, such as an open-heart procedure. The surgeon may inject the biological material into the necrotic tissue or proximate to the necrotic tissue. The surgeon may also deliver the biological material through the coronary vasculature. In practice, implanted cells have been observed to migrate, so over time some biological material transplanted in infarct region 14 may migrate outside infarct region 14. In addition, biological material transplanted in infarct region 14 may migrate to a different site inside infarct region 14.

In FIG. 1, repopulated zone 15 surrounds infarct region 14, and can include part or all of infarct region 14. In a typical patient, repopulated zone 15 may have a perimeter about a centimeter (0.4 inch) around the necrotic tissue. The invention is not limited to cases in which repopulated zone 15 completely surrounds infarct region 14, however.

At least two electrodes 20 and 22 are deployed epicardially proximate to repopulated zone 15. In particular, electrodes 20 and 22 are deployed such that a line between electrodes 20 and 22 substantially follows direction of contraction of natural cardiac muscle fibers. Electrodes 20 and 22 are deployed so that an electrical stimulation delivered to the epicardium via electrodes 20 and 22 creates a difference in electrical. potential, which in turn generates an electrical field that captures contractile fibers in repopulated zone 15. In other words, electrodes 20 and 22 are deployed to cause the contractile fibers in repopulated zone 15 to contract in a direction that aids hemodynamic function. A current flows from one electrode to the other, generally by ionic conduction along the surface of the tissue, rather than by gap junction propagation.

Transplanted contractile biological material tends to orient itself in the direction in which the tissue stretches. Accordingly, the contractile fibers of the transplanted material generally will, with time, align with nearby cardiac muscle fibers.

It is not necessary to the invention that all transplanted biological material contributes to contraction. Undifferentiated cells, for example, may undergo differentiation in response to stimulation, and may develop contractile capability. Also, some transplanted biological material may support the contractile biological material. Endothelial cells, for example, may promote vascularization in repopulated zone 15, and genetic material may promote differentiation or phenotypic conversion of other cells.

Electrodes 20 and 22 are coupled via leads 24 and 26 to an implantable medical device (IMD) (not shown in FIG. 1). The IMD generates one or more electrical stimuli, which are delivered to the epicardium via electrodes 20 and 22.

In FIG. 1, pacing and sensing leads are deployed in the chambers of heart 10 to monitor heart 10 and to administer pacing, defibrillation or other therapies to heart 10. The pacing and sensing leads may be coupled to the same IMD as leads 24 and 26, or may be coupled to a different IMD. For purposes of simplicity, it will be assumed that the pacing and sensing leads are coupled to the same IMD as leads 24 and 26.

An atrial lead 28 extends from the IMD through the superior vena cava 30 and into the right atrium 32. The distal end of atrial lead 28 includes one or more pace/sense electrodes 34. A ventricular lead 36 extends from the IMD through superior vena cava 30, through right atrium 32 and into the right ventricle 38. The distal end of ventricular lead 36 includes one or more pace/sense electrodes 40. Electrodes 34 and 40 may be bipolar or unipolar. Although shown in FIG. 1 as deployed inside the chambers of heart 10, the leads may be deployed epicardially, endocardially, intravascularly or in any combination thereof.

In the example depicted in FIG. 1, the IMD is configured to generate pacing stimulations, which are delivered to right atrium 32 or right ventricle 38 via pace/sense electrodes 34 and 40. In addition, the IMD senses electrical activity in heart 10 via electrodes 34 and 40. In particular, the IMD detects atrial and ventricular activations via electrodes 34 and 40. Electrodes 34 and 40 may be coupled to sense amplifiers that detect whether electrical activity exceeds a sensing threshold. In this way, the IMD detects P-waves indicative of atrial activation and R-waves indicative of ventricular activation. The IMD may also detect T-waves via electrodes 34 and 40, which indicate ventricular repolarization that occurs at the completion of ventricular contraction.

The IMD may also apply digital signal analysis to signals sensed via electrodes 34 and 40. The signals may be amplified and converted to multi-bit digital signals by an analog-to-digital (A/D) converter. A microprocessor may employ digital signal analysis techniques for various purposes, such as to classify the patient's heart rhythm or to analyze the morphology of the signals. During digital signal analysis, various cardiac parameters may be measured, such as the duration of the QRS complex and the Q-T interval.

Atrial lead 28 or ventricular lead 36 or both may include a defibrillation electrode to deliver defibrillation therapy under the control of the IMD. Defibrillation electrodes are desirable because patients who receive stimulations to repopulated zone 15 are at risk of fibrillation. Defibrillation electrodes provide added safety in light of this risk. Atrial and ventricular leads 28, 36 may also include other sensors, such as sensors that respond to the blood pressure inside heart 10.

Figure 2:
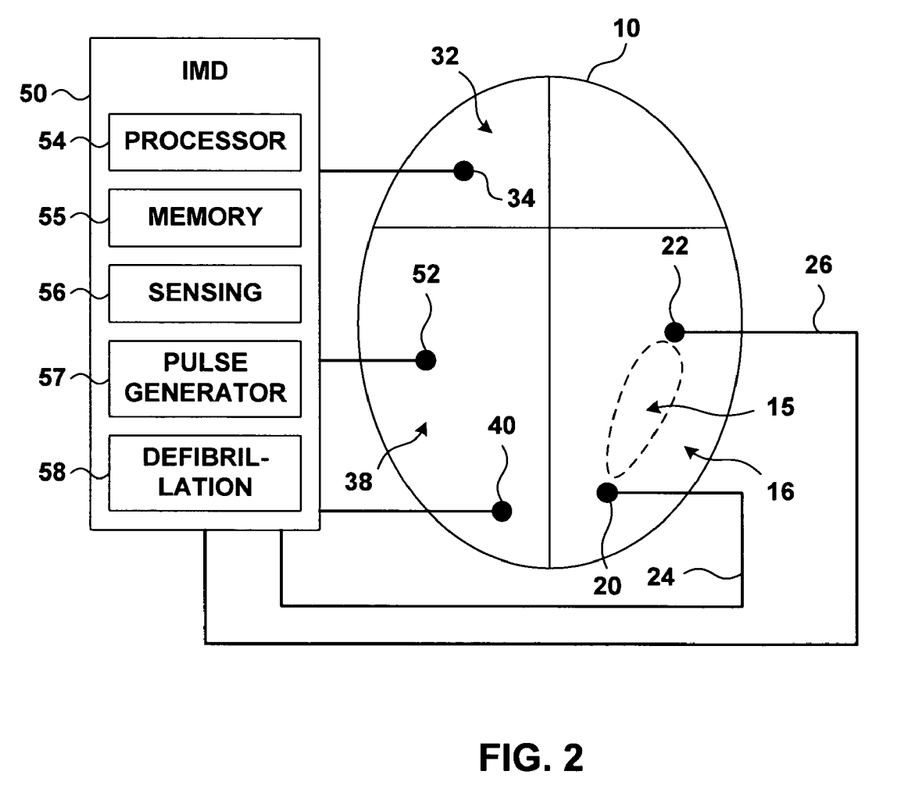
FIG. 2 is a block diagram showing a system that can electrically stimulate biological material transplanted in a myocardium.

FIG. 2 is a symbolic diagram of heart 10 with an IMD 50. IMD 50 controls delivery of electrical stimulation to repopulated zone 15 via electrodes 20 and 22. IMD 50 further senses atrial and ventricular activity via electrodes 34 and 40, and may also deliver pacing therapy to heart 10 via electrodes 34 and 40. In addition, IMD 50 receives signals from a sensor 52. Sensor 52 may be any sensor that detects any signal reflecting physiological activity. In general, sensor 52 may be selected to detect the stage of the cardiac cycle of heart 10. Sensor 52 may be, for example, an electrode disposed on the epicardium, or a pressure sensor deployed inside right ventricle 38, or a sound sensor deployed at any site in the body where heart sounds can be detected. Sensor 52 may also be, for example, a lead tip accelerometer that senses the wall motion of heart 10 in one, two or three dimensions. Sensor 52 may be, but need not be, deployed on ventricular lead 36 shown in FIG. 1. Sensor 52 may also include a plurality of sensors, such as intracardiac impedance sensors that detect changes in impedance that occur during the cardiac cycle.

IMD 50 includes at least one processor 54 that that regulates delivery of electrical stimulation to repopulated zone 15, and that further supervises pacing and defibrillation operations. Processor 54 comprises, for example, any microprocessor, digital signal processor, application specific integrated circuit or full custom integrated circuit.

Processor 54 determines whether heart 10 is in the ejection phase of the cardiac cycle, and causes electrical stimulation to be delivered to repopulated zone 15 during the ejection phase. Processor 54 may, for example, store a signal from sensor 52 in memory 55 and analyze the stored signal. Processor 54 may analyze a pressure signal, for example, to identify an occurrence at which a maximum change of sensed pressure in the ventricle occurs during a cardiac cycle. This analysis technique will be described in more detail below. Memory 55 may comprise any combination of volatile and non-volatile memory.

Processor 54 may also analyze electrical signals received via electrodes 20, 22, 34 or 40 and sensed via a sensing module 56 such as a peak sense and threshold measurement circuit. In particular, processor 54 can use the sensed electrical signals to determine whether heart 10 is in the ejection phase.

Processor 54 includes one or more pulse generators 56 to deliver stimulations repopulated zone 15 under the control of processor 54. Pulse generator 56 may also serve as pacer output circuitry, generating pacing pulses to be delivered to right atrium 32 and right ventricle 38 by electrodes 34 and 40, under the control of processor 54. Processor 54 may use pacing pulses from pulse generator 57 to determine whether heart 10 is in the ejection phase.

IMD 50 further includes a defibrillation module 58 delivers defibrillation or cardioversion therapy under the control of processor 54. Defibrillation module 58 delivers high-energy shocks to heart 10 when heart 10 exhibits a dangerous arrhythmia. As noted above, defibrillation capability is not necessary to the invention, but is desirable. The occurrence of an acute myocardial infarction is often associated with sudden cardiac death caused by ventricular arrhythmias, and the ventricular arrhythmias can be effectively terminated by defibrillation therapy.

In one embodiment of the invention, IMD 50 controls the rhythm of heart 10 by administering pacing stimulations via atrial electrode 34 and ventricular electrode 40. IMD 50 further administers stimuli proximate to repopulated zone 15 via epicedial electrodes 20 and 22. IMD administers stimuli via electrodes 20 and 22 to coincide with the pumping action of heart 10. More specifically, IMD 50 administers stimuli via electrodes 20 and 22 when the pulmonary and aortic valves of heart 10 are open.

The stimuli administered via electrodes 20 and 22 can cause tissue in or proximate to repopulated zone 15 to contract in synchrony with other cardiac tissue. In particular, the stimuli cause the biological material transplanted in and proximate to repopulated zone 15 to contract. The stimuli generally do not cause scar tissue in infarct region 14 to contract.

The response of various biological materials to stimulation is currently a subject of research. There is evidence that electrical stimulation of some kinds of biological material can cause the biological material to assume characteristics of muscle tissue. The biological material may, for example, show signs of differentiation, or may exhibit indications of phenotypic conversion, such as increased numbers of mitochondria, greater fatigue resistance or enhanced contractile properties. Some biological material, after repeated stimulation, begins to take on characteristics of muscle, such as skeletal muscle. It is believed possible that electrical stimulation of biological material may cause differentiation into cardiac muscle, which couples to the host tissue. In other words, ongoing research may include supplanting scar tissue with living contractile tissue. In addition, electrical stimulation may promote proliferation of the transplanted cells, thereby repopulating infarct region 14 with contractile tissue.

For purposes of describing the invention, however, it is assumed that at least a portion of the transplanted biological material contracts in some fashion in response to electrical stimulation from electrodes 20 and 22. It is not necessary that the biological material supplant scar tissue. It is not necessary for the invention that all transplanted biological material be contractile, or that the transplanted biological material be contractile upon transplantation. Rather, some transplanted biological material may be non-contractile when implanted, and may become contractile at the transplant site in response to stimulation. Also, it is not necessary for the invention that the transplanted biological material assume any particular characteristics or phenotype.

As noted above, the invention is not limited to any particular biological material or materials. For purposes of illustrating the invention, it will be assumed that the transplanted biological material in and proximate to infarct region 14 has characteristics of skeletal muscle. In other words, the biological material contracts in response to electrical stimulation, but need not contract in the same way as cardiac muscle. In general, skeletal muscle contracts and relaxes more rapidly than cardiac muscle. Skeletal muscle contracts and relaxes within ten to thirty milliseconds, but cardiac muscle contracts and relaxes within about a hundred milliseconds. Accordingly, IMD 50 delivers a set of stimuli to the biological material to cause the biological material to contract and relax in a manner similar to cardiac muscle. In other words, IMD 50 delivers a set of stimuli to the biological material to cause the biological material to contribute to the pumping action of heart 10.

The set of stimuli is delivered at a time in the cardiac cycle when contraction of the biological material contributes to hemodynamic function. In the example depicted in FIGS. 1 and 2, in which infarct region 14 and repopulated zone 15 are on the left ventricle, IMD 50 delivers the stimuli to coincide with the ventricular activation and pumping. The duration, timing and other characteristics of the set of stimuli depend upon the location of the biological material.

Figure 3:
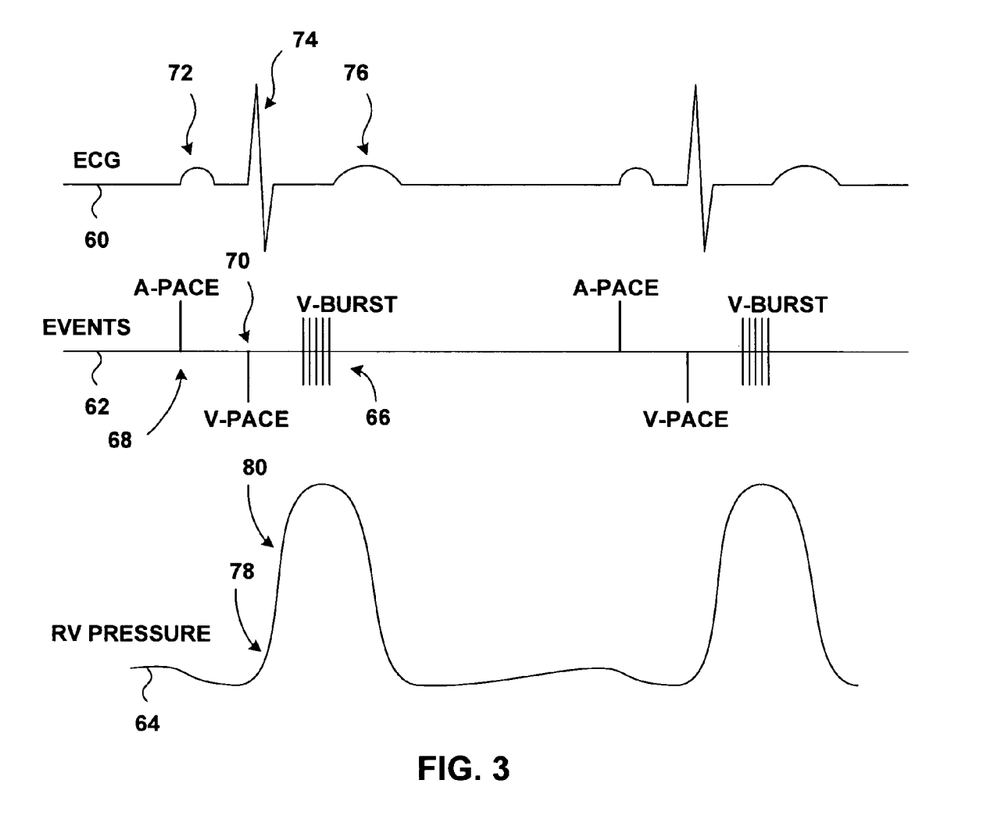
FIG. 3 is a timing diagram illustrating signals and the timing of electrical stimulation according to various embodiments of the invention.

FIG. 3 is a timing diagram illustrating techniques for delivery of stimuli to the transplanted biological material. FIG. 3 includes three signals. An electrocardiogram (ECG) 60 shows the electrical activity of heart 10. ECG 50 may be sensed with electrodes deployed on the body of the patient, including electrodes deployed epicardially or endocardially. An event marker 62 shows electrical stimulations delivered under the control of IMD 50. A pressure waveform 64 shows pressure inside a ventricle of heart 10, which may be measured by a pressure sensor deployed in right ventricle 38.

IMD 50 delivers a set of stimuli, identified as "V-Burst" 66, to the biological material. The characteristics of the set of stimuli will be described in more detail below. In addition, IMD delivers an atrial pacing pulse, identified as "A-Pace" 68, and a ventricular pacing pulse, identified as "V-Pace" 70. In the example shown in FIGS. 1 and 2, epicardial electrodes 20 and 22 deliver V-Burst 66. Electrodes 34 and 40 deliver A-Pace 68 and V-Pace 70.

In response to delivery of A-Pace 68, the atria of heart 10 depolarize. The depolarization manifests as a P-wave 72 in ECG 60. Delivery of V-Pace 70 causes the ventricles of heart 10 to depolarize, which manifests in ECG 60 as the QRS complex 74. Repolarization of the ventricles manifests in ECG 60 as T-wave 76.

IMD 50 delivers V-Burst 66 at a time when contraction of transplanted cells in repopulated zone 15 will assist in hemodynamic function. In addition, IMD 50 avoids delivering V-Burst 66 at a time when heart 10 is vulnerable to induction of arrhythmias. In the example shown in FIGS. 1 and 2, V-Burst 66 may aid the pumping function during contraction of the ventricles, and in particular, when the ejection phase begins and the aortic and pulmonary valves are open.

Delivery of V-Burst 66 at other times in the cardiac cycle would provide lesser hemodynamic assistance, or no hemodynamic assistance at all. Delivery of V-Burst 66 prior to QRS complex 74 would not assist in hemodynamic function, because the ventricles would be resting rather than contracting. Delivery of V-Burst 66 during the isovolumetric contraction phase would generally provide little hemodynamic assistance, and may cause the biological material to become fatigued. Stimulating the biological material during repolarization would not only fail to aid hemodynamic function, but may generate a dangerous arrhythmia such as ventricular fibrillation. Accordingly, IMD 50 times the delivery of V-Burst 66 to take place when the aortic or pulmonary valves are open. In general, the valves are open during a portion of the S-T segment, i.e., at some time between the end of the QRS complex 74 and T-wave 76.

The invention encompasses timing the delivery of V-Burst 66 occur during the ejection phase, i.e., while the aortic and pulmonary valves are open and blood is being ejected from the ventricles. Various techniques exist for delivering V-Burst 66 at a time when heart 10 is in the ejection phase.

One technique is to deliver V-Burst 66 at an interval following an intrinsic cardiac event, or following an event under the control of IMD 50. For example, IMD 50 may deliver V-Burst 66 at time interval after the R-wave, which is the peak of QRS complex 74, or at a time interval following delivery of a ventricular pace 70. The time interval can be a function of several factors, such as the heart rate of the patient, or other factors that affect the S-T segment.

Another timing technique uses the pressure inside a ventricle as an indicator of whether a valve is closed or open. A pressure sensor may be deployed in right ventricle 38 or in left ventricle 16. In FIG. 3, it is assumed that a pressure sensor has been deployed in right ventricle 38. Pressure signal 64 reflects the sensed pressure.

In a cardiac cycle, ventricular depolarization causes ventricular contraction. For a short period, no blood leaves the ventricles, and the contraction of the ventricles is isovolumetric. During isovolumetric contraction, the pressure in the ventricles builds, but is insufficient to force blood through the pulmonary or the aortic valve. On pressure signal 64, the onset of isovolumetric contraction is reflected in a sharp upturn 78 of pressure signal 78.

When the pressure in right ventricle 38 overcomes the pressure in the pulmonary arteries, the blood drives the pulmonary valve open, and right ventricle 38 ejects blood into the pulmonary arteries. When the pulmonary valve opens, contraction is no longer isovolumetric. Pressure in right ventricle 38, although still increasing due to ventricular contraction, increases at a slower rate. As a result, there is an inflection point 80 in right ventricular pressure signal 80 when the pulmonary valve opens. Inflection point 80 represents the point of maximum change of pressure with time. In right ventricular pressure signal 64, inflection point 80 is the point of maximum slope.

Inflection point 80 may be found by analysis of pressure signal 64. For example, IMD 50 may find the maximum value the first derivative of pressure signal 64, or a corresponding zero crossing in the second derivative of pressure signal 64. By sensing the inflection point or the maximum change in pressure, the time of ejection from right ventricle 38 can be identified.

A similar process occurs in left ventricle 16, and a signal from a pressure sensor in left ventricle 16 may be analyzed in a similar fashion to determine the time that the pressure forces open the aortic valve. For many patients, deployment of a pressure sensor in right ventricle 38 can adequately identify the opening of both the pulmonary and aortic valves, because both valves typically open at about the same time.

In this way, by identifying an occurrence at which a maximum change of sensed pressure in a ventricle occurs, IMD 50 can detect when heart 10 enters the ejection phase. IMD 50 delivers V-Burst 66 during the ejection phase.

In a typical embodiment, IMD 50 need not analyze a pressure sensor signal with every cardiac cycle. Instead, IMD 50 may deliver V-Burst 66 at an interval following an intrinsic or paced cardiac event, and may perform pressure signal analysis from time to time to determine whether the interval causes stimulation to take place during the ejection phase.

The invention is not limited to timing stimulations as a function of intrinsic cardiac events, paced cardiac events, or pressures. Other sensors and signals can be used to detect the opening of a pulmonary or aortic valve, or to estimate reliably when the valves are open. An accelerometer, a flow meter, an intracardiac impedance sensor or a sonomicrometer, for example, may generate a signal that can be used to detect whether the heart is in the ejection phase. A microphone that detects heart sounds also may detect the onset of isovolumetric contraction by detecting the closure of the atrioventricular valves. Identifying the onset of isovolumetric contraction may be used for accurately estimating when heart 10 is in the ejection phase.

In general, V-Burst 66 comprises a series of distinct stimulations. The amplitude, pulse width, number of stimulations and interval between stimulations may vary as a function of the biological material stimulated and the response. These stimulation parameters may be adjusted for a particular patient, e.g., to enhance cardiac volume or cardiac synchrony. In general, V-Burst 66 should deliver sufficient energy to excite the tissue, but not so much energy as to unnecessarily drain the power supply or damage the tissue.

Figure 4:
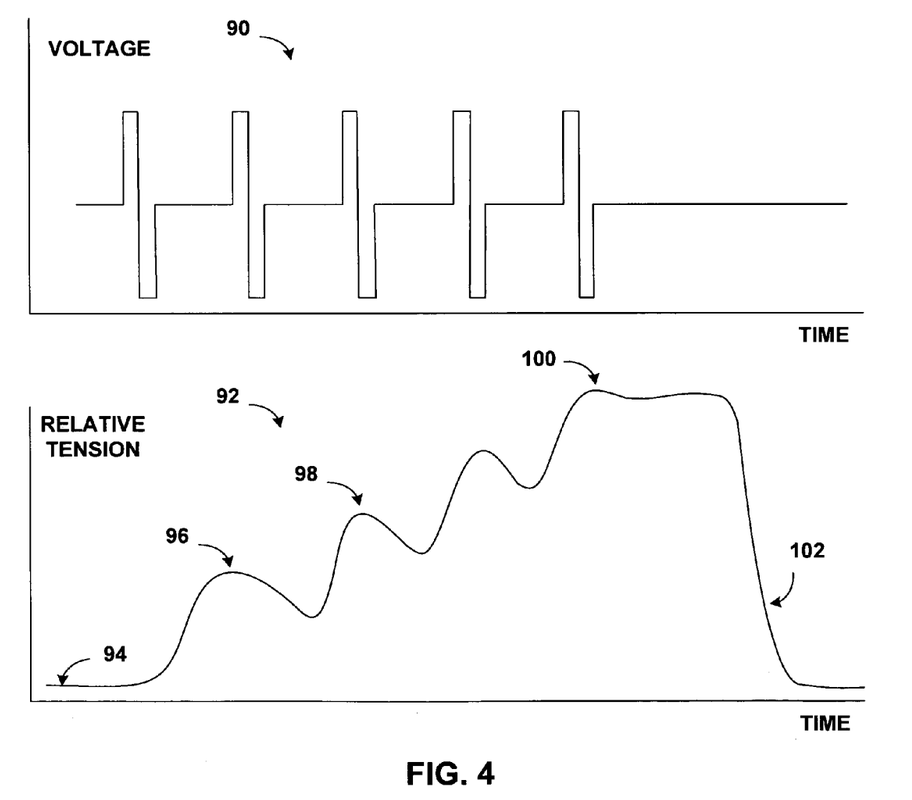
FIG. 4 is timing diagram illustrating a set of pacing stimulations and a corresponding response of transplanted biological material having contractile properties of skeletal muscle.

FIG. 4 illustrates an exemplary V-Burst 90 comprising five bipolar pulses having square wave shapes. Each pulse has an amplitude above the threshold potential of the contractile material in repopulated zone 15. The amplitude of the voltage depends upon the number of contractile fibers affected, which depends upon the distance between stimulating electrodes 20 and 22. For example, the amplitude of the voltage can be about one volt per millimeter of separation between electrodes 20 and 22. V-Burst 90 may include one pulse every one hundredth of a second, and each pulse may have a pulse width of a millisecond. Generally speaking, the shape of the waveform is not as important as the energy it provides to the tissue, because the stimuli ought to be strong enough to excite the newly formed contractile tissue. Also, the stimulation waveform should typically be charge-balanced, meaning that positive and negative charges cancel following each pulse. Charge-balancing prevents harm to the tissue surrounding the electrodes. It is not necessary, however, that the positive and negative segments of the pulse have the same shape or duration.

In an application in which the biological material includes skeletal muscle, the pulses of exemplary V-Burst 90 come one after another, and do not allow the muscle to relax fully after each pulse. A graph of contractile activity 92 shows that, upon stimulation, muscle tension increases from a relaxed state 94 to a peak 96, and then begins to decline. Before the muscle can relax fully, however, another stimulating pulse causes a summation response 98, increasing the tension further or maintaining the tension. Additional stimulating pulses can cause a sustained tetanic contraction 100. When the stimulation ends, the tension returns 102 to a resting state.

The effect of stimulating the biological material with a set of stimuli is to cause the skeletal muscle cells to contract for a longer time than skeletal muscle cells would ordinarily contract. In other words, the effect is to cause skeletal muscle cells to have a contraction time comparable to that of cardiac muscle cells. In the time shortly after transplantation of the biological material, stimulation therapy can be suspended for some cardiac cycles to allow the tissue to recover and to build a tolerance to fatigue. For example, the stimulation may be delivered on every fifth cardiac cycle shortly after transplantation, with the frequency of stimulation increasing over time.

In addition, stimulation therapy can be suspended from time to time so that IMD 50 or another device can monitor the hemodynamic function of heart 10. IMD 50 or another device may monitor, for example, hemodynamic parameters such as cardiac output, stroke volume, ventricular pressure, blood flow rate and the like. By such monitoring, IMD 50 or another device can gather data that indicate whether or not the transplanted tissue is contributing to hemodynamic function when stimulated. The data may indicate, for example, that the transplanted biological material is ineffective in contributing to hemodynamic operation, in which case stimulation therapy may be discontinued to conserve power for other functions, such as defibrillation or pacing. When the transplanted biological material is ineffective in contributing to hemodynamic operation, physician intervention, such as intervention to transplant new biological material, may also be indicated. The data may also indicate that or that the biological material has become integrated with the native myocardium, in which case stimulation therapy may be reduced to allow the new tissue to be excited intrinsically via the endogenous conduction system of heart 10. Stimulation therapy may be reduced by delivering electrical stimulation at a reduced per-cardiac-cycle frequency, such as by delivering one set of stimulating pulses for every five cardiac cycles instead of one set of stimulating pulses for every cardiac cycle. The data may also indicate that continued stimulation therapy is appropriate.

Figure 5:
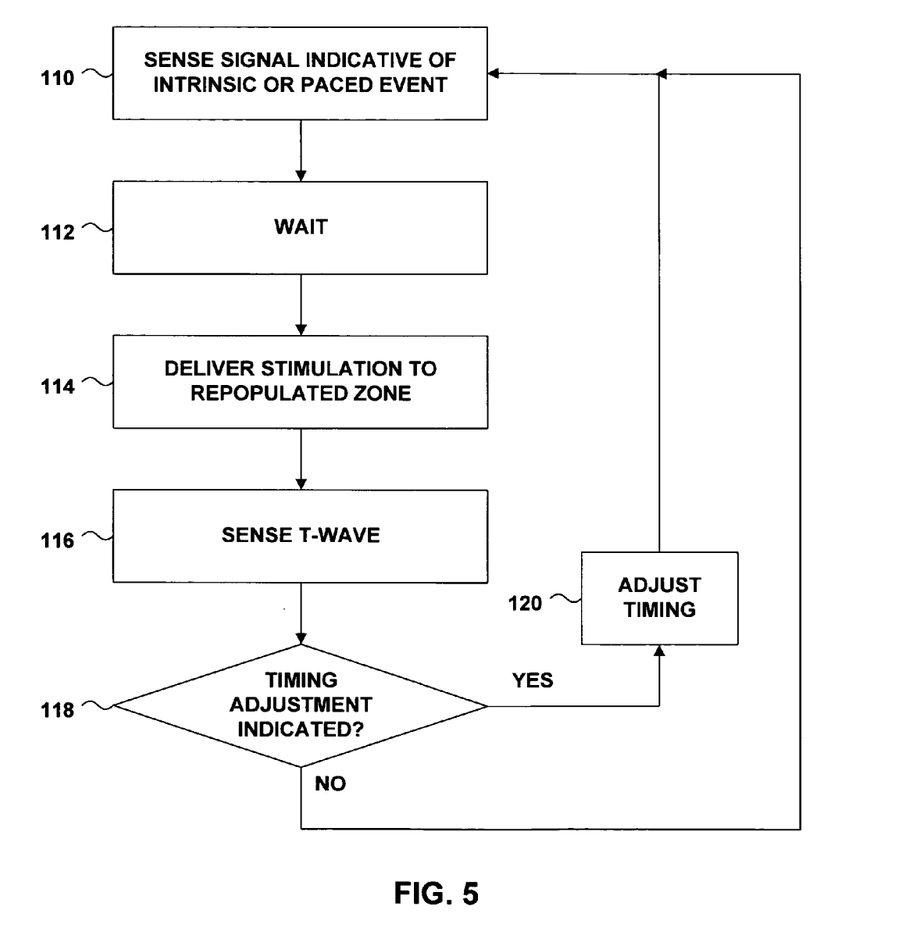
FIG. 5 is a flow diagram illustrating a technique for timing the delivery of electrical stimulation.

FIG. 5 is a flow diagram illustrating an embodiment of the invention. IMD 50 senses one or more signals indicative of an intrinsic or paced cardiac event (110). The sensed signal may include a biological signal, such as a pressure signal, a signal responsive to motion, an electrical signal or a heart sound signal. The signal may also correspond to a pacing event, such as the delivery of a ventricular pace. Depending upon the sensed signal, IMD 50 may wait for a time interval (112) for heart 10 to enter the ejection phase, and then IMD 50 delivers stimulation to the repopulated zone (114). IMD 50 times the delivery of stimulation (114) to coincide with the ejection phase of heart 10.

In one embodiment of the invention, the waiting interval (112) may be eliminated. When the signal indicative of a cardiac event is a ventricular pressure signal, for example, IMD 50 may deliver stimulation (114) promptly upon sensing the maximum change of pressure, with no waiting. Analysis of a pressure signal with every cardiac cycle may result in signal processing that drains the power supply for IMD 50, however.

In a typical embodiment, however, IMD 50 senses at least one signal indicative of a cardiac event on each cardiac cycle, and senses other signals less frequently. In an illustrative application, IMD 50 senses the R-wave sense amplifiers on every cardiac cycle (110), waits for a time interval after the R-wave (112), and delivers a stimulation at a time when heart 10 is expected to be in the ejection phase (114). When sensing an R-wave with a sense amplifier consumes less power than pressure signal analysis, it can be more efficient to time the delivery of stimulations with respect to the sensed R-wave. Pressure signal analysis may be still be performed periodically to assure that stimulation is taking place during the ejection phase, but pressure signal analysis need not be performed on every cardiac cycle.

IMD 50 may further sense the T-wave (116). As noted above, the stimulation should generally take place while the aortic and pulmonary valves are open, and the valves are generally closed by the time the T-wave occurs. By monitoring the T-wave (116), IMD 50 verifies that the stimulation (114) takes place during the S-T segment, and that the stimulation does not take place when heart 10 is vulnerable to induction of arrhythmias. The T-wave may be, but need not be, monitored on every cardiac cycle.

From time to time, IMD 50 may determine whether the stimulations are being delivered at an appropriate time (118). Such a determination may be based upon signals such as pressure signals and T-wave monitoring signals, which can indicate whether the waiting period after R-wave detection is appropriate, or too short or too long. When a timing adjustment is needed, IMD 50 increases or decreases the waiting period (120). IMD 50 may check the timing (118) periodically, such as after a fixed number of cardiac cycles, or in response to an event, such as an increase in heart rate, or both.

The various embodiments of the invention may result in one or more advantages. While necrotic tissue is less elastic than healthy cardiac tissue, transplantation of biological material can improve the elasticity of the heart. In addition, necrotic tissue adversely affects hemodynamic function, but transplantation of biological material, combined with electrical stimulation, can restore some pumping ability to a damaged region of heart tissue.

In addition, the invention can complement other treatments for myocardial infarction. Coronary artery bypass, for example, can address providing a blood supply to heart tissue, but does not address the effects of scar tissue upon the elasticity and the pumping ability of the heart. The invention, however, can address those concerns.

The following example, which demonstrates some of the aspects of the invention, is for illustrative purposes. The subjects of the tests included nine canines.

Three canines formed the control group and six canines formed the "test" or "treatment" group. Skeletal muscle biopsies of approximately 5 grams were obtained from all animals from the masseter muscle for the isolation of skeletal muscle cells, or "satellite" cells. Details of a procedure to isolate and culture satellite cells are described in Chiu R C-J et al., "Cellular Cardiomyoplasty: Myocardial Regeneration With Satellite Cell Implantation.," *Ann. Thorac. Surg.* 60:12-8 (1995).

Approximately two weeks after the biopsy procedure, myocardial infarction was induced in all animals by temporary occlusion of the left anterior descending (LAD) coronary artery followed by reperfusion. This technique is described in Kao R L et al., "Satellite Cell Transplantation to Repair Injured Myocardium," *Card. and Vasc. Regener.* 1:31-42 (2000). Following the infarction/reperfusion, animals in the control group received injections of culture medium (Sigma), and animals in the treatment group received $5 \times 10^7$ autologous satellite cells via intra-myocardial injection. Six weeks after the initial surgery, the animals were anesthetized, the chest was opened, and the instruments for physiologic measurement of the cardiovascular function were placed. Intravascular pressure catheters (Millar Instruments, Inc., Houston, Tex.) were advanced into the left ventricle and flow probes (Transonic System, Inc., Ithaca, N.Y.) were placed around the aorta.

All nine of the animals in the study were subjected to cardiovascular functional studies, during which the myocardium received electrical stimulation. The hemodynamic function of the heart of each animal was assessed before the animals received the electrical stimulation.

Unipolar epicardial leads were attached to the atrium and the ventricle to pace both chambers of the heart. Rib spreaders used in the surgery served as the return electrode for the unipolar pacing pulses sent to the atrium and the ventricle. Two more epicardial electrodes were attached to the myocardium, near the perimeter of the infarct region, which were used to deliver bipolar stimulation to the skeletal muscle formed in the infarct region. The epicardial electrodes were placed such that the electrical field created by these electrodes was perpendicular to the muscle fiber orientation, which allowed the capture of maximum number of fibers in the repopulated zone. All five leads, atrial and ventricular stimulation lead, return electrode connected to the rib spreader and the two leads going to the infarct zone were attached to a custom stimulator designed for the study.

The pacemaker portion of this custom stimulator provided stimulation pulses in DOO mode, meaning that both chambers were paced at all times, with no sensing of the intrinsic activation, and without any inhibition of the pacing. The pacing rate and the paced atrioventricular delay were chosen to be slightly higher than the intrinsic rate of the animal to overdrive the sinoatrial node and to assure that the pacemaker solely governed the timing of the atrial and ventricular contractions. The output amplitude of the stimulator was adjusted until capture of both chambers of the heart could be verified from the monitored surface ECG. Measured physiologic parameters, such as aortic flow and left ventricular pressure, while a DOO pacing was applied, formed the baseline for subsequent measurements.

Referring to FIG. 2, each animal received an atrial electrode 34 disposed in right atrium 32 and a ventricular electrode 40 disposed in right ventricle 38. Each animal further received stimulating electrodes 20 and 22 proximate to the region that had received the culture medium (in the case of the control group) or the satellite cells (in the case of the test group). Electrodes 20 and 22 were about 50 millimeters apart.

Referring to FIG. 3, each animal received an atrial pace 68, a ventricular pace 70 and a V-Burst 66. As noted above, the ECG 60 of each animal was monitored.

Because the satellite cells placed in or proximate to the infarct region were obtained from skeletal muscles having a fast twitch response, the stimulation included a train of five pulses in V-Burst stimulation 66. The duration of V-Burst stimulation 66 was 41 milliseconds. The object of delivering a set of pulses was to cause a long duration contraction of the skeletal muscle formed in the repopulated zone, which would augment the systolic function produced by the healthy native myocardium. The burst stimulation was applied in bipolar mode, i.e., between electrodes 20 and 22. The object of bipolar stimulation was to reduce the unintentional stimulation of the surrounding skeletal muscles of the chest.

Each pulse within the burst train was cathodic (negative) for one millisecond, anodic (positive) for eight milliseconds, and the stimulation circuitry was designed to remove all the charges left on the tissue during the cathodic stimulation by using the anodic pulse. Timing of the burst stimulation was determined using the ventricular stimulation pulse of the DOO pacer as a reference. Also, care was taken to adjust the timing of the burst stimulation to prevent the stimulation from coinciding with T-wave 76 and the vulnerable period of the cardiac cycle, to reduce the chance of inducing ventricular fibrillation. The amplitude of the pulses, and the delay between delivery of the ventricular pace and the burst train, were independently controlled.

Left ventricular blood pressure and aortic blood flow measurements were repeated during the application of the DOO pacing combined with burst stimulation, and were used to measure the added benefit from the stimulated contraction of the skeletal muscle in the repopulated zone. Mean arterial pressure was estimated as a function of diastolic and systolic pressures. Aortic output multiplied by mean arterial pressure yielded cardiac power, and cardiac power was indicative of hemodynamic function.

The data collected concerning hemodynamic function showed that hearts in the test group maintained an elastic structure, while the infarct regions of the hearts in the control group gained more plastic properties. The transplanted cells enhanced the elasticity of the heart, while the fibrous scar tissue in the control group did not.

When the amplitude of the pulses was at or above fifty volts (i.e., one volt per millimeter of electrode separation), and the delay between delivery of the ventricular pace and the burst train was about fifty milliseconds or longer, the power exhibited by the left ventricle showed considerable improvement, in comparison to the same animal when it was not stimulated with a burst train. Three out of six animals in the treatment group showed improvement in cardiac power when paced and stimulated with a burst train, with the improvement being about forty-five to ninety percent, while three did not show significant improvement. In the control group, none of the animals showed improvement in cardiac power.

Following the measurement of cardiac function, the animals were sacrificed, and the hearts were removed for morphological and histological examinations. The results of the examinations showed that animals in the treatment group developed healthy looking muscle tissue at the site of satellite cell implantation. In the control animals, by contrast, the infarct region had abundant connective tissue formed by fibrin and collagen, without evidence of cardiomyocytes.

The preceding example is illustrative of an application of the invention, and the invention is not limited to the particular test protocols described above.

Moreover, the preceding specific embodiments are illustrative of the practice of the invention, and various modifications may be made without departing from the scope of the claims. For example, it is not necessary that a single device control pacing of the heart and delivery of stimulations to the repopulated zone. In one variation, a first device may be responsible for pacing and another device may be responsible for delivering stimulations to the repopulated zone.

In another variation, the patient may require no pacing, and the IMD may be a monitor, rather than a pacemaker. Such an IMD may sense intrinsic cardiac events, which can be used to time the delivery of the stimulations. In a further variation, the IMD may be a full-featured device, providing pacing such as atrial, right ventricular, left ventricular and bi-ventricular pacing. A full-featured device may further provide therapies such as cardioversion therapy, defibrillation therapy and anti-tachycardia pacing in addition to stimulation of the repopulated zone. The invention encompasses all of these variations.

The electrode and sensor placements shown in FIGS. 1 and 2 are exemplary, but the invention encompasses other deployments as well. For example, the electrodes that stimulate the repopulated zone may be deployed endocardially.

The electrodes may be deployed, for example, on the distal end of lead that enters the right ventricle, penetrates the septal wall, and fixes to the tissue in the left ventricle proximate to the infarct region. In another variation, the electrodes may be deployed in a vessel, via the coronary sinus and the great vein. Whether leads are deployed endocardially or via the coronary vasculature may depend upon whether the infarct region is accessible to such deployment. Some leads may include anticoagulation features.

The invention is not limited to any particular electrode placement. On the contrary, the stimulating electrodes would ordinarily be deployed according to the position and orientation of the infarct regain and repopulated zone of each individual patient. Although the examples in FIGS. 1 and 2 show damage to the left ventricle, the techniques of the invention may also be applied when there has been damage to the right ventricle, for example, or when there has been damage to the interventricular septum. Nor is the invention limited to any particular kind of electrodes or any particular technique or fixation mechanism for placing the electrodes. The electrodes may be, for example, small-surface-area electrodes or larger line electrodes sewn into the tissue, or electrodes deployed in patches applied to the tissue. The electrodes may include, for example, conventional metallic conductors or conductive polymers.

The invention is not limited to the particular stimulation schemes described herein. Different biological material may respond differently to electrical stimulation. Accordingly, an IMD may be programmed to apply a stimulation scheme that works best for the patient. In addition, the invention does not exclude other stimulation therapies. For example, the invention includes subthreshold stimulation, which delivers insufficient energy to the biological material to cause contraction, but which may promote neovascularization of the repopulated zone or infarct region.

The invention may be embodied in a computer-readable medium with instructions that cause a programmable processor to carry out the techniques described above. A "computer-readable medium" includes but is not limited to read-only memory, Flash memory, EPROM and a magnetic or optical storage medium. The medium may comprise instructions for causing a programmable processor to electrically stimulate biological material transplanted in a myocardium of a heart during an ejection phase of a cardiac cycle. These and other embodiments are within the scope of the following claims.

The invention claimed is:

1. A method comprising electrically stimulating biological material transplanted in a myocardium of a heart during an ejection phase of a cardiac cycle wherein said method further comprises sensing a pressure in a ventricle of a heart and wherein electrically stimulating the biological material transplanted in the myocardium comprises delivering a set stimulating pulses to the biological material in response to the pressure.

2. The method of claim 1, wherein the biological material comprises cells.

3. The method of claim 2, wherein the biological material comprises cells selected from skeletal myoblasts, differentiated stem cells, undifferentiated stem cells, fibroblasts, endothelial cells and genetically engineered cells.

4. The method of claim 1, wherein the biological material comprises genes.

5. The method of claim 1, wherein the biological material comprises a chemoattractant.

6. The method of claim 1, wherein electrically stimulating the biological material transplanted in the myocardium comprises electrically stimulating the biological material transplanted in an infarct region of the myocardium.

7. The method of claim 1, wherein electrically stimulating the biological material transplanted in the myocardium comprises electrically stimulating the biological material transplanted proximate to an infarct region of the myocardium.

8. The method of claim 1, further comprising: sensing a biological signal; and electrically stimulating the biological material in response to the biological signal.

9. The method of claim 8, wherein the biological signal comprises at least one of a blood pressure signal, a cardiac depolarization signal, cardiac repolarization signal, a cardiac impedance signal and a heart sound signal.

10. The method of claim 8, wherein the biological signal indicates whether the heart is in the ejection phase.

11. The method of claim 1, further comprising:
identifying an occurrence at which a maximum change of sensed pressure in the ventricle occurs during the cardiac cycle; and electrically stimulating the biological material during the cardiac cycle after the identified occurrence.

12. The method of claim 1, further comprising:
identifying, during a first cardiac cycle, a time interval between an occurrence of a cardiac event and a maximum change of sensed pressure in the ventricle during the first cardiac cycle; sensing the cardiac event in a second cardiac cycle; and electrically stimulating the biological material during the second cardiac cycle after the cardiac event and the time interval.

13. The method of claim 12, wherein the cardiac event is an R-wave.

14. The method of claim 12, further comprising adjusting the time interval as a function of an occurrence of the cardiac event and a maximum change of sensed pressure in the ventricle during in a third cardiac cycle.

15. The method of claim 1, wherein electrically stimulating the biological material comprises delivering a set of stimulating pulses to the biological material.

16. The method of claim 15, wherein the set of stimulating pulses comprises approximately five pulses.

17. The method of claim 15, wherein the set of stimulating pulses comprises bipolar square wave pulses.

18. The method of claim 15, wherein the stimulating pulses are delivered to the biological material by at least two electrodes separated by a separation distance, and wherein the set of stimulating pulses comprises pulses having a voltage amplitude of approximately one volt per millimeter of separation distance.

19. The method of claim 15, wherein the set of set of stimulating pulses comprises pulses separated by approximately one one hundredth of a second.

20. The method of claim 1, wherein electrically stimulating the biological material comprises electrically stimulating the biological material with energy sufficient to cause the biological material to contract, the method further comprising electrically stimulating the biological material with energy insufficient to cause the biological material to contract.

21. The method of claim 1, further comprising: identifying, during a first cardiac cycle, a time interval between an occurrence of a cardiac event and the ejection phase; sensing the cardiac event in a second cardiac cycle; and electrically stimulating the biological material during the second cardiac cycle after the cardiac event and the time interval.

22. The method of claim 21, wherein the cardiac event is an R-wave.

23. The method of claim 21, further comprising adjusting the time interval as a function of an occurrence of the cardiac event and the ejection phase in a third cardiac cycle.

24. A method comprising: electrically stimulating biological material transplanted in a myocardium of a heart during an ejection phase of a first cardiac cycle; suspending electrical stimulation of the biological material during the ejection phase of a second cardiac cycle; monitoring a hemodynamic parameter during the second cardiac cycle; and determining whether to electrically stimulate the biological material during the ejection phase of a third cardiac cycle as a function of the monitoring.

25. The method of claim 24, wherein the hemodynamic parameter comprises at least one of cardiac output, stoke volume, ventricular pressure and blood flow rate.

26. The method of claim 24, wherein determining whether to electrically stimulate the biological material during the ejection phase of the third cardiac cycle as a function of the monitoring comprises discontinuing electrical stimulation when the monitoring indicates that the biological material is ineffective in contributing to hemodynamic operation of the heart.

27. The method of claim 24, wherein determining whether to electrically stimulate the biological material during the ejection phase of the third cardiac cycle as a function of the monitoring comprises delivering electrical stimulation at a reduced per-cardiac-cycle frequency.

28. A computer-readable medium comprising instructions for causing a programmable processor to: control delivery of electrical stimulation of biological material transplanted in a myocardium of a heart during an ejection phase of a first cardiac cycle; suspend delivery of electrical stimulation of the biological material during the ejection phase of a second cardiac cycle; monitor a hemodynamic parameter during the second cardiac cycle; and determine whether to electrically stimulate the biological material during the ejection phase of a third cardiac cycle as a function of the monitoring, wherein the instructions that cause the processor to determine whether to electrically stimulate the biological material during the ejection phase of the third cardiac cycle as a function of the monitoring comprise instructions causing the processor to discontinue electrical stimulation when the monitoring indicates that the biological material is ineffective in contributing to hemodynamic operation of the heart.

29. The medium of claim 28, wherein the hemodynamic parameter comprises at least one of cardiac output, stroke volume, ventricular pressure and blood flow rate.

30. The medium of claim 28, wherein the instructions that cause the processor to determine whether to electrically stimulate the biological material during the ejection phase of the third cardiac cycle as a function of the monitoring comprise instructions causing the processor to control delivery of electrical stimulation at a reduced per-cardiac-cycle frequency.

31. A computer-readable medium comprising instructions for causing a programmable processor to: control delivery of electrical stimulation of biological material transplanted in a myocardium of a heart during an ejection phase of a first cardiac cycle; suspend delivery of electrical stimutation of the biological material during the ejection phase of a second cardiac cycle; monitor a hemodynamic parameter during the second cardiac cycle; and determine whether to electrically stimulate the biological material during the ejection phase of a third cardiac cycle as a function of the monitoring, wherein the instructions that cause the processor to determine whether to electrically stimulate the biological material during the ejection phase of the third cardiac cycle as a function of the monitoring comprise instructions causing the processor to control delivery of electrical stimulation at a reduced per-cardiac-cycle frequency.

32. The medium of claim 31, wherein the hemodynamic parameter comprises at least one of cardiac output, stroke volume, ventricular pressure and blood flow rate.

33. The medium of claim 31, wherein the instructions that cause the processor to determine whether to electrically stimulate the biological material during the ejection phase of the third cardiac cycle as a function of the monitoring comprise instructions causing the processor to discontinue electrical stimulation when the monitoring indicates that the biological material is ineffective in contributing to hemodynamic operation of the heart.

* * * * *

UNITED STATES PATENT AND TRADEMARK OFFICE
CERTIFICATE OF CORRECTION

PATENT NO. : 7,349,740 B2  
APPLICATION NO. : 10/896760  
DATED : March 25, 2008  
INVENTOR(S) : Orhan Soykan and Maura G. Donovan Page 1 of 1

It is certified that error appears in the above-identified patent and that said Letters Patent is hereby corrected as shown below:

Title Page  
(75) Inventors: Donovan G. Maura   should be   Maura G. Donovan

Col. 14, Line 55, Claim #1: ...the pressure.   should be ...the pressure and, wherein...cycle.

Col. 14, Line 65, Claim #5: ...a chemoattractant.   should be ...a chemo attractant.

Col. 15, Line 52, Claim #21: ...approximately one one...   should be   ...approximately one hundredth....

Signed and Sealed this  
Fourteenth Day of February, 2012

David J. Kappos  
*Director of the United States Patent and Trademark Office*